United States Patent [19]

Krasner

[11] Patent Number: 4,950,289
[45] Date of Patent: Aug. 21, 1990

[54] SMALL INCISION INTRAOCULAR LENS WITH ADJUSTABLE REFRACTIVE POWER

[75] Inventor: Gary N. Krasner, Irvine, Calif.

[73] Assignee: CooperVision, Inc., Palo Alto, Calif.

[21] Appl. No.: 925,909

[22] Filed: Nov. 3, 1986

[51] Int. Cl.⁵ .......................... A61F 2/16; A61F 9/00; A61B 17/00
[52] U.S. Cl. ......................................... 623/6; 606/107
[58] Field of Search ............... 623/6, 7, 8; 128/303 R, 128/321; 606/107

[56] References Cited

U.S. PATENT DOCUMENTS

| | | | |
|---|---|---|---|
| 3,919,724 | 11/1975 | Sanders et al. | 623/8 |
| 4,073,014 | 2/1978 | Poler | 623/6 |
| 4,253,199 | 3/1981 | Banko | 623/6 |
| 4,373,218 | 2/1983 | Schachar | 623/6 |
| 4,512,040 | 4/1985 | McClure | 623/6 |
| 4,573,998 | 3/1986 | Mazzocco | 623/6 |
| 4,575,373 | 3/1986 | Johnson | 623/6 |
| 4,585,457 | 4/1986 | Kalb | 623/6 |
| 4,596,578 | 6/1986 | Kelman | 623/6 |
| 4,600,004 | 7/1986 | Lopez et al. | 128/303 R |
| 4,608,049 | 8/1986 | Kelman | 623/6 |
| 4,615,702 | 10/1986 | Koziol et al. | 623/6 |
| 4,619,256 | 10/1986 | Horn | 128/303 R |
| 4,619,662 | 10/1986 | Juergens, Jr. | 623/6 |
| 4,669,464 | 6/1987 | Sulepov | 128/303 R |
| 4,681,102 | 7/1987 | Bartell | 128/303 R |
| 4,704,122 | 11/1987 | Portnoy | 623/6 |

FOREIGN PATENT DOCUMENTS 0190056 8/1986 European Pat. Off. ................ 623/6
2124500A 2/1984 United Kingdom ................ 623/6

OTHER PUBLICATIONS

"The Bartel Injector for Soft-IOL Implantation"; Ocular Surgery News; Evan D. Jones, M.D.; pp. 28 & 29; Aug. 1, 1986.

Primary Examiner—Ronald L. Frinks
Attorney, Agent, or Firm—Vorys, Sater, Seymour & Pease

[57] ABSTRACT

An intraocular lens which is compressible to fit through a small ocular incision into the eye and whose refractive power is adjustable once the inserted lens has been reformed and remedially positioned in the eye. The lens includes a deformable soft optic, a translucent collar encircling the soft optic and attached to it at fixed spaced points, and haptics attached to the collar for remedially positioning the soft optic in the eye. The collar has a separation or break to define two collar arms. When the collar is compressed the arms slide relative to one another to narrow the collar, and the compressed lens can then be inserted in the eye. Once in the eye the collar is released and the arms reformed together to form a rigid circle supporting the soft optic. The soft optic is formed by a transparent bag having a thickened perimeter and filled with a transparent fluid. When the lens is in place in the eye, a fine needle can be inserted into the eye and into the bag perimeter. The amount of fluid in the bag is altered through the needle and the refractive power of the soft optic thereby adjusted as needed.

96 Claims, 2 Drawing Sheets

SMALL INCISION INTRAOCULAR LENS WITH ADJUSTABLE REFRACTIVE POWER

BACKGROUND OF THE INVENTION

The present invention relates to intraocular lenses, and more particularly to intraocular lenses which can be inserted through small incisions into the eye. It further relates to intraocular lenses whose refractive power can be altered while positioned in the eye.

Intraocular lenses have gained wide acceptance recently in the replacement of human crystalline lenses after a variety of cataract removal procedures. One current treatment of cataracts is to surgically remove them through ultrasonic emulsificiation, so that the light can once again reach the retina. When the natural lens is removed to eliminate the cataract it may be replaced by an artificial lens. The preferred method for restoring vision is an aphakic patient is to surgically implant a lens, a so-called intraocular lens, within the eye. Such a lens, however, need not and generally is not removed. Also, since the intraocular lens is positioned in approximately the same position as the natural lens, it provides vision correction without undue magnification of the image.

A problem associated with the proper implantation of intraocular lenses is the accurate determination of the precise refractive power required for them. Based on measurements of the prescriptive power of the patient's natural lens and measurement of the depth of the eye, a relatively accurate determination can be made of the proper refraction or power of the intraocular lens to be placed in the patient's eye. In most cases, the aphakic patient can have an intraocular lens implanted which provides good distance visual acuity even though spectacles may be required for reading since the intraocular lens cannot change its refraction or power like a natural lens. However, in some cases the intraocular lens may not provide good distance visual acuity. Since an intraocular lens cannot be readily removed and a new intraocular lens with a different power surgically implanted without unduly jeopardizing the patient's vision, the patient must rely on spectacles to provide good distance visual acuity.

A disadvantage of conventional rigid intraocular lenses is that implantation of the lens requires a relatively large, often six to nine millimeters, incision in the ocular tissue, and present methods of cataract removal by phacoemulsification require only a 3.5 mm incision which may be closed with a single suture. This long incision surgical procedure can lead to relatively high complication rates, such as increased risks of infection, retinal detachment, and lacerations of the ocular tissues, particularly with respect to the pupil. Small incision intraocular lenses do exist though and examples of them include soft foldable silicone lenses, foldable silicone optics with conventional non-foldable haptics, hydrogel lenses which are inserted into the eye in a dry miniature state and which then absorb ocular fluid to expand to their full size, and rigid materials with an optic divided into three sections wherein the outer two nontransparent sections slide under the central transparent one to compress the size of the optic. Each has its disadvantages though including stability problems. Thus, a need has arisen for an improved small incision intraocular lens, whose refractive power is adjustable after implantation.

OBJECTS OF THE INVENTION

Accordingly, it is a principal object of the present invention to provide a novel intraocular lens construction.

Another object of the invention is to provide an improved intraocular lens design which can be inserted through a small incision in the ocular tissue.

A further object of the invention is to provide a novel intraocular lens designed to minimize the time required to surgically implant it.

A still further object of the invention is to provide an improved intraocular lens whose refractive power can be adjusted while in place in the eye.

Another object is to provide an improved fluid-filled intraocular lens which does not sag or deform under the effects of gravity.

A further object is to provide an improved method for implanting intraocular lenses through small ocular incisions.

A still further object is to provide a novel method of altering the corrective power of an implanted intraocular lens which can be done quickly and with a minimum of trauma to the eye.

Another object is to provide an improved method of surgically implanting intraocular lenses through incisions generally less than 3.5 mm, which reduces the chances for induced astigmatism.

Other objects and advantages of the present invention will be more apparent to those skilled in the art from the accompanying description taken in conjunction with the accompanying drawings.

DETAILED DESCRIPTION OF THE PREFERRED EMBODIMENTS

Figure 1:
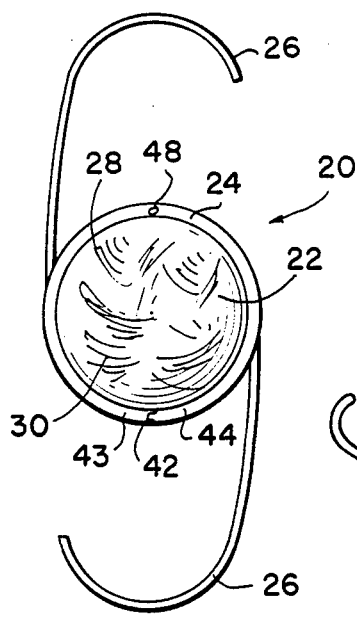
FIG. 1 is a front perspective view of a small incision intraocular lens of the present invention.

Referring to the drawings, a small incision intraocular lens of the present invention is illustrated generally at 20. Lens 20 very simply comprises a soft optic 22, a generally rigid circular collar 24 attached to and surrounding the soft optic, and a pair of J-shaped haptic loops 26 attached to and extending out from the collar. Many other types of haptics are currently available and may be used in the present lens.

Figure 9:
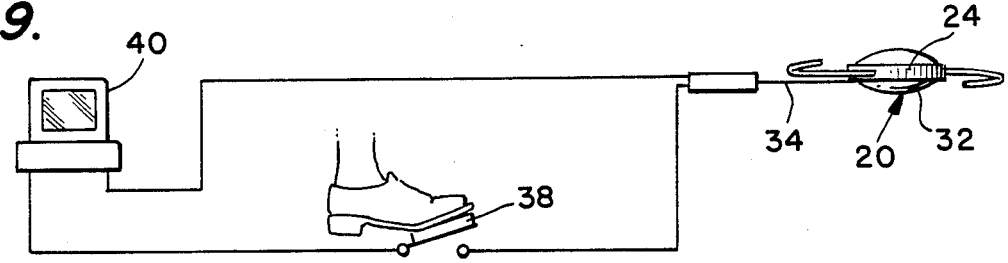
FIG. 9 is a schematic of the needle system of the present invention provided for adjusting the amount of fluid in the lens of FIG. 1.

Soft optic 22 is formed from a transparent sac or bag 28 adapted to be filled with a transparent fluid 30. Optic bag 28 is biocompatible with ocular fluids, transparent and can be formed of any suitable material such as polypropylene, polyethylene or silicone. Bag 28 is impermeable to fluids to prevent exchange of fluids between the bag and the eye. Also, since injected air bubbles in the bag would be troublesome, bag 28 should be constructed of a gas permeable material. Bag 28 is provided with a thickened peripheral portion 32 which serves two functions. First, greater support and stability for attachment of the soft optic to the collar is provided. Second, it forms a thicker edge providing for a self-sealing capability of small punctures, including punctures made by a fine needle, such as shown in FIG. 9 at 34, for adjusting the amount of fluid 30 in bag 28. The presence of thicker perimeter 32 of the bag around its entire circumference allows the surgeon to pierce bag 28 at any point on the periphery of the lens to adjust the fluid therein, unlike a valving arrangement which provides limited accessibility. This gives greater flexibility to the adjustment procedure and provides accessibility after surgery. Further, the wound made by needle 34 does not require suturing and is similar to the wound made by a needle used to perform a secondary posterior capsulotomy.

When filled with fluid 30, bag 28 defines an artificial lens suitable for intraocular replacement of the natural lens. Either bag 28 or fluid 30 may have a higher refractive index than the fluids of the eye. If fluid 30 has the higher refractive power, the thickness of optic 22 dictates the power; if bag 28 has the power, fluid 30 separates the two lenses (front and back of bag 28) and specifies the power. In the latter case, fluid 30 may be a balanced salt solution similar to that used to irrigate the eye during surgery. Silicone oil is a candidate for a refracting fluid. If fluid 30 comprises a gel, the gel should not polymerize or otherwise harden; it is to be a liquid so that some of it can be easily added or removed from the optic to change the refractive power of the lens.

Optic 22 preferably has a biconvex shape. This is the natural lens shape and can produce a very good optical resolution, minimize the effects of internal reflections, and minimize the problems of spherical aberration. For the present adjustable lens 20 this shape is desirable because the adding or removing of fluid 30 has its greatest effect on the central surfaces of optic 22, since the central surfaces of a lens are the locations of the first contact of incoming light rays.

It is also within the scope of the present invention to provide a fluid filled bag similarly constructed as bag 28, which acts on its own as a lens within a nearly intact, natural capsular bag. The bag would be inserted empty and filled during surgery, and post-operative adjustments can then be made. This type of lens can also be used in focusable optical systems such as in microscopes, cameras, and binoculars.

Collar 24 is generally rigid thereby stabilizing fluid filled optic 22 so it does not sag or deform with gravity. It is attached to optic 22, for example, by a plurality of spaced spot welds, preferably four welds 36. Collar 24 is translucent so that it will not transmit light and create a possible double image on the patient's retina. This translucent property also allows the surgeon to easily identify the edge of optic 22 should changes in its liquid volume be required. Collar 24 can be made, for example, of polypropylene or PMMA (polymethyl methacrylate).

Figure 3:
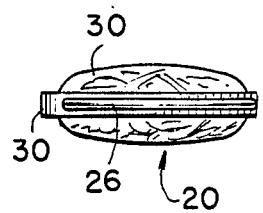
FIG. 3 is an end elevational view of the lens of FIG. 1.
Figure 2:
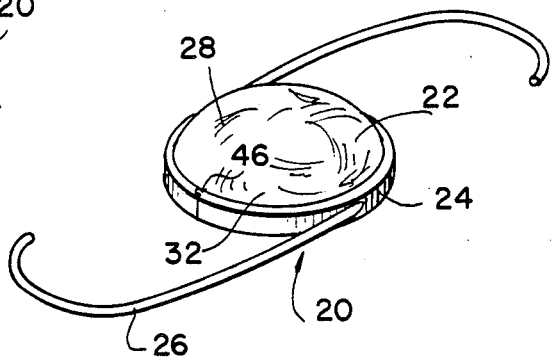
FIG. 2 is a perspective view of the lens of FIG. 1.

The haptics of lens 20 are shown constructed as conventional J-shaped loops 26 and typically are constructed of either polypropylene or PMMA. Loops 26 stabilize and center optic 22 within the eye with respect to the pupil. Loops 26 are anchored at their proximal ends in the collar 24, as shown in FIG. 2. By the orientation of loops 26 it is possible under one construction of the lens, by vaulting optic 22 slightly from the posterior capsule due to the configuration of the haptics angling from the collar towards the posterior capsule, to keep the optic from resting on the posterior capsule of the eye. In other words, referring to FIG. 3, both of the haptics would angle downwardly generally below the bottom surface of the optic. This vaulted design would make secondary capsulotomy easier. This lens closely resembles current posterior chamber intraocular lenses, but the haptics are more stable than soft haptics of the prior art lenses. In an alternative construction depicted in FIG. 3 the haptics extend generally radially from the collar. The surfaces of the optic protrude above and below the collar and thus the collar does not contact the posterior capsule when the lens is implanted in the posterior chamber. The optic in contact with the capsule may prevent cell migration to the central posterior capsule. If this construction is thereby effective in preventing posterior capsule opacification, secondary capsulotomy by YAG laser or invasive surgery would not be required.

Bag 28 may be filled at the factory for a specified refractive power, or partially filled at the factory and finished in surgery, or inserted empty and completely filled in the operating room. It is further within the scope of the present invention to provide an automated filling system, as illustrated schematically in FIG. 9, which allows the surgeon to concentrate on positioning needle 34 in the intraocularly positioned lens through the thickened lens perimeter 32 while a foot control pump 38 slowly delivers the fluid through the needle into it. Further, a minicomputer 40 can be provided to take the refractive data of lens 20 and determine the amount of fluid to be injected into bag 28. Minicomputer 40 (or other control means) can also control the fluid injection rate and amount so that the surgeon can then concentrate on placing and holding needle 34 in bag 28 without applying excessive pressure, to insure a more accurate system and a reduction of the surgical time.

Figure 4:
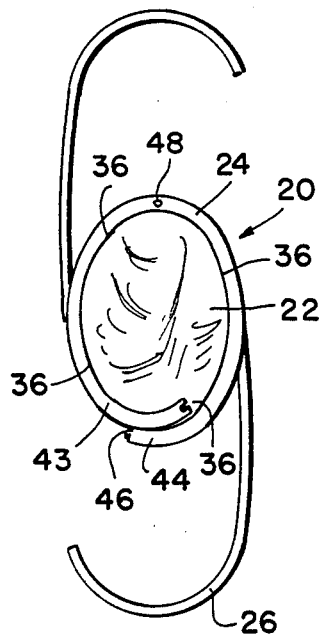
FIG. 4 is a view similar to FIG. 1 illustrating the lens in its compressed condition.

Collar 24 has a separation or break, as shown in FIG. 1 at 42, to define first and second collar arms or sides 43, 44. This allows the surgeon to compress lens 20 by depressing one side 43 of collar 24 at the separation and sliding it under the opposite side 44, as best illustrated in FIG. 4. Collar 24 and optic 22 are thereby narrowed to enable them to pass through smaller ocular incisions. Soft optic 22 will thereby be wrinkled temporarily but otherwise not affected. By spot welding bag 28 to collar 24 and not attaching it completely around the circumference of the bag, soft optic 22 can be compressed, and the depressed collar side 43 will slide to the point of the first spot weld 36. After being compressed and inserted in the eye by instrumention, which is described later, lens 20 is released in the eye and the collar sides 43, 44 repositioned to reform the rigid circular configuration of the collar. In this configuration a locking mechanism, such as is shown in FIGS. 2 and 4 at 46, locks the arms together in place. This locking mechanism can take the form of a dovetail relationship of the collar sides. In lieu of a locking mechanism, a straight split in the collar is sufficient according to one embodiment of the invention. It further is within the scope of the present invention to provide positioning holes 48 in collar 26 in which tools can be inserted for handling and manipulating lens 20.

Figure 5:
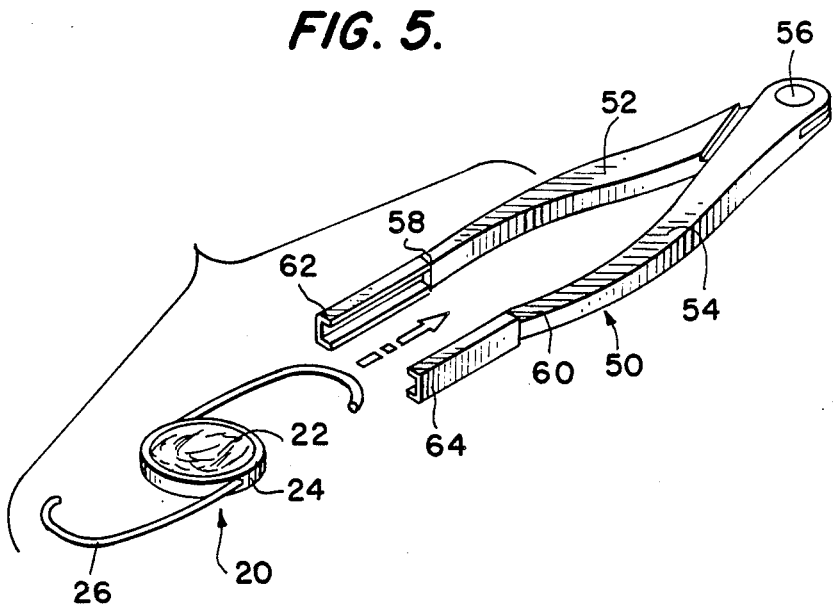
FIG. 5 is a perspective view of the lens of FIG. 1 being inserted in a manipulating instrument of the present invention.
Figure 6:
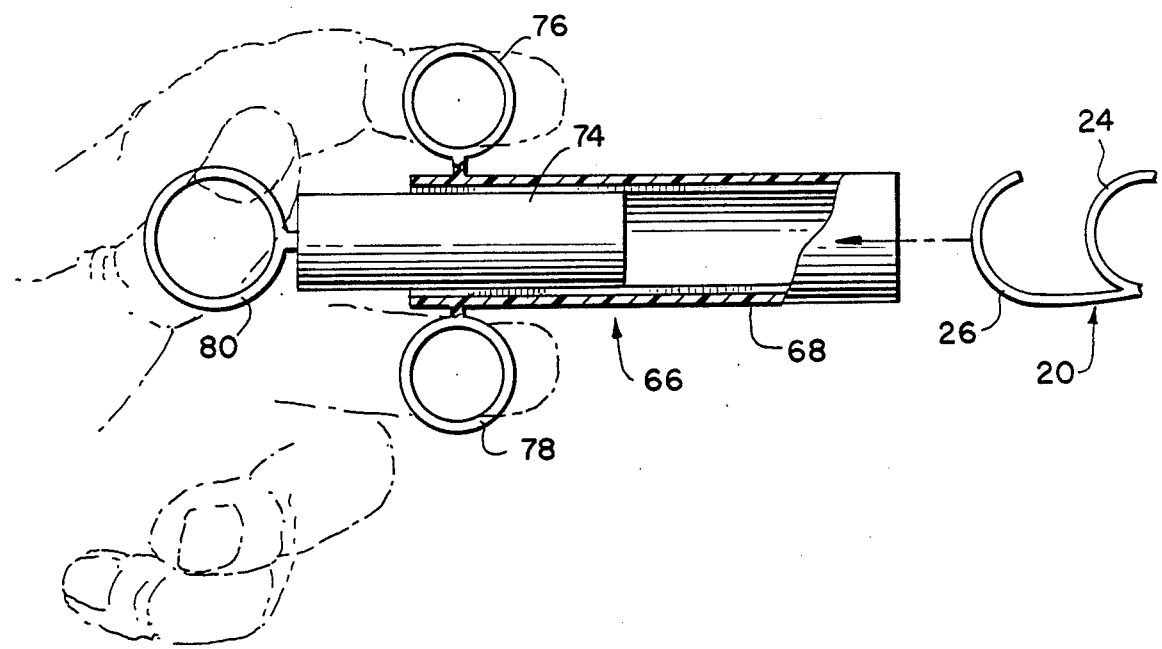
FIG. 6 is a front view of an insertion tool of the present invention wherein the lens of FIG. 1 is illustrated being inserted therein.
Figure 7:
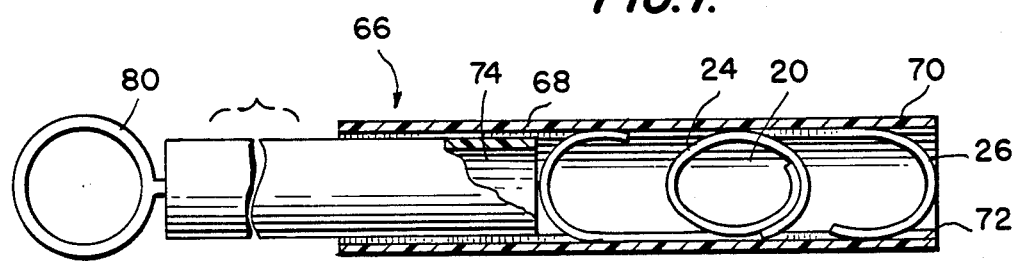
FIG. 7 is a fragmentary view of the forward portion of the insertion tool of FIG. 6 illustrating the lens of the present invention inserted therein in its compressed condition.

The present invention further defines a specially configured instrument, for handling and/or compressing the lens, as best shown in FIG. 5, generally at 50. Referring thereto instrument 50 is shown to have a forcep type of construction with first and second arms 52, 54 joined at one end 56 and their opposite ends 58, 60 being provided, respectively, with oppositely disposed box-shaped channels 62, 64 configured for holding collar 24 between them. When the collar is positioned between channels 62, 64, arms 52, 54 can be compressed together to compress the lens into its narrowed shape, as shown in FIG. 4, and then inserted as illustrated by the arrow in FIG. 6 into an insertion tool 66 and positioned therein as shown in FIG. 7 to be positioned entirely within insertion tool 66 or with its tip extending out from it. In lieu of the pin attachment at end 56 the arms 52 and 54 can be welded together as in conventional forceps.

Figure 8:
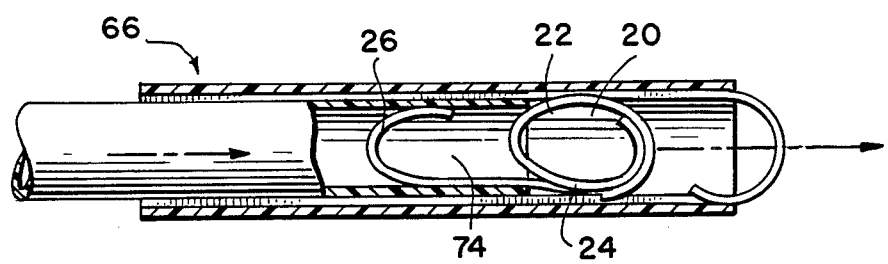
FIG. 8 is a view similar to FIG. 7 illustrating the slider member engaging the compressed lens and pushing it for ejection from the insertion tool.

Insertion tool 66 comprises a rectangular shaped tubular member 68 having oppositely facing channels 70, 72 in which collar 24 is inserted. A slider member 74 of the tool slides in the channels and is configured with a low profile, as best shown in FIG. 8, to preferably pass entirely underneath haptic loop 26 and directly engage collar 24 for accurate control of the ejection of lens 20 from the tool into the eye. Although depicted in the drawings as being tubular, the preferred configuration of slider member 74 is flat; it is a flat sheet with proximal thumb loop or ring 80 attached to it to fit under haptic 26 and push against collar 24 to thereby move the lens. Insertion tool 66 includes a pair of oppositely placed finger rings 76, 78 on the sides of tubular member 68 and a third finger ring 80 attached to the end of slider member 74 for controlling its sliding movement as best shown by the hand illustrated with phantom lines in FIG. 6. These rings are similar to the rings on certain hypodermic syringes provided to ease manipulations of them.

Tubular member 68 is a rectangular tube approximately 3.0 mm wide and 0.5 mm high with a central portion of one flat surface 82 (the top) missing. The internal rectangle defined by tubular member 68 may have its sharp corners rounded. Lens 20 held in the surgeon's finger, or in the compressing instrument 50, is lubricated with VISCOAT or other visco-elastic substance and inserted into the distal (or proximal) end of the tube. (Alternatively the lens can be inserted in an uncompressed state into a modified insertion tool and the tool compresses it, as well as controllably inserts it, as by pushing it through and out a narrowing channel.) The surgeon slides lens 20 to the desired point, either completely within tubular member 68 or with the forward haptic part of the lens extended. The central portion of the top of the tubular member is omitted so that the surgeon can then use an instrument to position lens 20 in the tubular member from above. The upper opening also allows the surgeon to lubricate the lens from above, to position it within the tube, and to lift the haptic of the lens so that the slider member can pass under it.

By ejecting the compressed intraocular lens 20 slowly and controllably into the eye as is possible with insertion tool 66, the lens resumes its natural shape without "springing open" within the eye and possibly causing injury. Tool 66 can place the lens in the same position as the manual technique employed with current lenses. The lens is manipulated into its remedial position in either the anterior or posterior chambers of the eye. Fluid 30 then is added or withdrawn from bag 28 through needle 34 inserted into the periphery 32 of the bag. Lens 20 is thus quickly, safely and easily inserted through a small incision into the eye and its refractive power adjusted during the implantation surgery and/or at a later time as needed.

From the foregoing detailed description, it will be evident that there are a number of changes, adaptations, and modifications of the present invention which come within the province of those skilled the art. However, it is intended that all such variations not departing from the spirit of the invention be considered as within the scope thereof as limited solely by the claims appended hereto.

What is claimed is:

1. A small incision intraocular lens comprising:
   a deformable soft optic,
   a collar positioned generally about said soft optic and compressible about an axis thereof to fit through a small incision into the eye and then expandable when in the eye,
   an attaching means for attaching said collar to said soft optic,
   a haptic means attached to said collar for remedially positioning said soft optic in the eye after having been inserted therein,
   said collar being broken so that a first collar side can slide relative to a second collar side when said collar is compressed, and
   said collar including a locking means for locking said first and second collar sides together when said collar is in its expanded state.

2. The intraocular lens of claim 1 wherein said haptic means comprises at least two spaced haptics extending out from said collar.

3. The intraocular lens of claim 3 wherein said haptics comprise at least two J-shaped loops.

4. The intraocular lens of claim 2 wherein said haptics comprise at least two flexible, resilient loops attached at their proximal ends to said collar.

5. The intraocular lens of claim 1 wherein said collar is rigid, generally circular and positioned about the periphery of said soft optic.

6. The intraocular lens of claim 1 wherein said collar includes two collar ends which overlap when said collar is compressed and are in generally abutting relation when said collar is in a relaxed state.

7. The intraocular lens of claim 1 wherein said attaching means attaches the inner surface of said collar directly to the outer surface of said soft optic.

8. The intraocular lens of claim 1 wherein said attaching means comprises a welding means.

9. The intraocular lens of claim 1 wherein said attaching means comprises a plurality of attachments spaced about said collar.

10. The intraocular lens of claim 9 wherein said attachments comprise spot welds.

11. The intraocular lens of claim 1 wherein said soft optic has a biconvex configuration.

12. The intraocular lens of claim 1 wherein said soft optic has a thickened perimeter.

13. The intraocular lens of claim 1 wherein said collar is translucent.

14. The intraocular lens of claim 1 further comprising a means for changing the power of said soft optic when in the eye.

15. The intraocular lens of claim 1 further comprising a means for changing the thickness of said soft optic when in the eye.

16. The intraocular lens of claim 1 further comprising a means for altering the corrective power of said soft optic when said haptic means is positioning said soft optic in the eye.

17. The intraocular lens of claim 1 wherein said collar is sufficiently compressible so that said intraocular lens will pass through an ocular incision having a length generally not greater than three and one half millimeters.

18. The intraocular lens of claim 1 wherein said soft optic is constructed of polypropylene, polyethylene or silicone.

19. The intraocular lens of claim 1 wherein said soft optic comprises a fluid-filled sac.

20. The intraocular lens of claim 1 wherein said soft optic comprises a bag filled with a pliable substance.

21. The intraocular lens of claim 20 wherein said pliable substance is inert and optically transparent.

22. The intraocular lens of claim 20 wherein said pliable substance is a liquid.

23. The intraocular lens of claim 20 wherein said pliable substance is a liquid gel which does not polymerize or otherwise harden.

24. The intraocular lens of claim 20 wherein said pliable substance comprises a polymeric liquid material of gel-like consistency.

25. The intraocular lens of claim 20 wherein said bag is formed of a fluid-impervious, flexible, transparent material.

26. The intraocular lens of claim 1 further comprising a device including a needle adapted to pass through the eye and into said soft optic when remedially positioned in the eye for varying the amount of fluid in said soft optic to thereby alter its corrective power.

27. The intraocular lens of claim 26 wherein said soft optic includes a portion through which said needle passes and is adapted to self seal about the puncture opening created by said needle, as said needle is removed from said soft optic.

28. The intraocular lens of claim 27 wherein said portion is thicker than adjacent portions of said soft optic.

29. The intraocular lens of claim 27 wherein said portion is about the periphery of said soft optic, and adjacent to said collar.

30. The intraocular lens of claim 27 wherein said soft optic is filled with a fluid which is transparent, biocompatible with the fluids of the eye, and has a specific gravity generally not greater than aqueous.

31. The intraocular lens of claim 1 wherein said haptic means is adapted to position said soft optic off of the posterior capsule of the eye when said soft optic is remedially positioned in the posterior chamber of the eye.

32. The intraocular lens of claim 1 further comprising a compressing means engageable with opposite sides of said collar for compressing said collar so that said lens can be compressed and inserted through a small incision into the eye.

33. The intraocular lens of claim 1 further comprising an injecting means for inserting said lens when compressed into the eye and releasing it once in the eye.

34. The intraocular lens of claim 33 further comprising a lens inserting means for inserting said lens in a compressed condition into said injecting means.

35. The intraocular lens of claim 34 wherein said lens inserting means comprises an instrument including a pair of opposed channels adapted to engage opposite sides of said collar and a moving means for moving said opposed channels towards each other to compress said collar held therebetween.

36. The intraocular lens of claim 35 wherein said moving means comprises manually operated forceps.

37. The intraocular lens of claim 35 wherein said opposed channels are box-shaped.

38. The intraocular lens of claim 34 further comprising a lubricant lubricating said collar while held by said inserting means and before being inserted into said injecting means.

39. The intraocular lens of claim 1 wherein said collar is expandable when in the eye about said axis.

40. The intraocular lens of claim 34 further comprising a lubricant for lubricating said collar.

41. The intraocular lens of claim 40 wherein said lubricant comprises a visco-elastic substance.

42. The intraocular lens of claim 33 wherein said injecting means includes a tube configured to hold said collar in its compressed condition and a sliding member positioned in said tube for sliding said compressed collar out of said tube.

43. The intraocular lens of claim 42 wherein said injecting means includes a pair of finger rings attached to said tube and said sliding member further comprises a finger ring attached to said sliding member.

44. The intraocular lens of claim 42 wherein said sliding member passes underneath said haptic means to directly engage said collar.

45. The intraocular lens of claim 42 wherein said tube has an upper opening providing access to a lens positioned in said tube.

46. The intraocular lens of claim 33 wherein said haptic means comprises a pair of opposed haptic loops, and said injecting means positions said loops along the axis of lens ejection.

47. The intraocular lens of claim 1 wherein said collar is rigid and formed from polypropylene or polymethyl methacrylate, and said haptic means is anchored in said rigid collar.

48. The intraocular lens of claim 1 wherein said soft optic comprises a bag and fluid at least partially filling said bag.

49. The intraocular lens of claim 48 wherein said collar stabilizes said soft optic so that said soft optic is not significantly deformed by gravity and so that the edges of said soft optic do not waver in the fluid of the eye.

50. The intraocular lens of claim 1 wherein said locking means includes a dovetail arrangement of said first and second collar sides.

51. A small incision intraocular lens comprising:
a deformable soft optic comprising a bag containing a pliable substance,
a collar positioned generally about said soft optic and compressible about an axis thereof to fit through a small incision into the eye and then expandable when in the eye, said collar comprising two collar ends which overlap when said collar is compressed and are in generally abutting relation when said collar is in a relaxed state, an attaching means for attaching said collar to said soft optic, and a haptic means attached to said collar for remedially positioning said soft optic in the eye after having been inserted therein.

52. The intraocular lens of claim 51 wherein said collar is rigid, generally circular and positioned about the periphery of said soft optic.

53. The intraocular lens of claim 51 wherein said attaching means attaches the inner surface of said collar directly to the outer surface of said soft optic.

54. The intraocular lens of claim 51 further comprising a means for changing the power of said soft optic when in the eye.

55. The intraocular lens of claim 51 wherein said pliable substance is insert and optically transparent.

56. The intraocular lens of claim 51 wherein said pliable substance is a liquid.

57. The intraocular lens of claim 51 wherein said pliable substance is a liquid gel which does not polymerize or otherwise harden.

58. The intraocular lens of claim 51 wherein said pliable substance comprises a polymeric liquid material of gel-like consistency.

59. The intraocular lens of claim 51 wherein said bag is formed of a fluid-impervious, flexible, transparent material.

60. The intraocular lens of claim 51 further comprising a device including a needle adapted to pass through the eye and into said soft optic when remedially positioned in the eye for varying the amount of fluid in said soft optic to thereby alter its corrective power.

61. The intraocular lens of claim 51 further comprising an injecting means for inserting said lens when compressed into the eye and releasing it once in the eye, and a lens inserting means for inserting said lens in a compressed condition into said injecting means.

62. The intraocular lens of claim 61 wherein said soft optic comprises a bag and fluid at least partially filling said bag, and said collar stabilizes said soft optic so that said soft optic is not significantly deformed by gravity and so that the edges of said soft optic do not waver in the fluid of the eye.

63. A small incision intraocular lens comprising:
a deformable soft optic,
a collar positioned generally about said soft optic and compressible about an axis thereof to fit through a small incision into the eye and then expandable generally about said axis when in the eye,
an attaching means for attaching said collar to said soft optic,
said attaching means attaching the inner surface of said collar directly to the outer surface of said optic,
a haptic means attached to said collar for remedially positioning said soft optic in the eye after having been inserted
a device including a needle adapted to pass through the eye and into said soft optic when remedially positioned in the eye for varying the amount of fluid in said soft optic to thereby alter its corrective power.

64. The intraocular lens of claim 63 wherein said soft optic includes a portion through which said needle passes and is adapted to self seal about the puncture opening created by said needle, as said needle is removed from said soft optic.

65. The intraocular of claim 64 wherein said portion is thicker than adjacent portions of said soft optic.

66. The intraocular lens of claim 64 wherein said portion is about the periphery of said soft optic, and adjacent to said collar.

67. The intraocular lens of claim 63 wherein said collar is translucent.

68. The intraocular lens of claim 63 further comprising an injecting means for inserting said lens when compressed into the eye and releasing it once in the eye, and a lens inserting means for inserting said lens in a compressed condition into said injecting means.

69. A small incision intraocular lens comprising:
a deformable soft optic,
a translucent collar positioned generally about said soft optic and compressible about an axis thereof to fit through a small incision into the eye and then expandable generally about said axis when in the eye,
an attaching means for attaching said collar to said soft optic,
a haptic means attached to said collar for remedially positioning said soft optic in the eye after having been inserted therein, and
a device including a needle adapted to pass through the eye and into said soft optic when remedially positioned in the eye for varying the amount of fluid in said soft optic to alter its corrective power.

70. The intraocular lens of claim 69 wherein said soft optic includes a portion through which said needle passes and is adapted to self seal about the puncture opening created by said needle, as said needle is removed from said soft optic.

71. The intraocular lens of claim 70 wherein said portion is thicker than adjacent portions of said soft optic, and said portion is about the periphery of said soft optic, and adjacent to said collar.

72. A small incision intraocular lens system comprising:
a deformable soft optic,
a collar positioned generally about said soft optic and compressible about an axis thereof to fit through a small incision into the eye and then expandable generally about said axis when in the eye,
an attaching means for attaching said collar to said soft optic,
said attaching means attaching the inner surface of said collar directly to the outer surface of said soft optic,
a haptic means attached to said collar for remedially positioning said soft optic in the eye after having been inserted therein,
an injecting means for inserting said lens when compressed into the eye and releasing it once in the eye, and
a lens inserting means for inserting said lens in a compressed condition into said injecting means.

73. The intraocular lens system of claim 72 wherein said lens inserting means comprises an instrument including a pair of opposed channels adapted to engage opposite sides of said collar and a moving means for moving said opposed channels towards each other to compress said collar held therebetween.

74. The intraocular lens system of claim 73 wherein said moving means comprising manually-operated forceps.

75. The intraocular lens system of claim 72 wherein said injecting means includes a tube configured to hold said collar in its compressed condition and a sliding member positioned in said tube for sliding said compressed collar out of said tube.

76. The intraocular lens of claim 75 wherein said member passes underneath said haptic means to directly engage said collar.

77. The intraocular lens system of claim 75 wherein said tube has an upper opening providing access therethrough to a lens positioned therein.

78. The intraocular lens system of claim 72 wherein said haptic means comprises a pair of opposed haptic loops, and said injecting means positions said loops along the axis of lens ejection.

79. An intraocular lens comprising: a deformable soft optic, a collar positioned about said soft optic, an attaching means for attaching said collar to said soft optic, and a haptic means attached to and extending out from said collar for remedially positioning said soft optic in the eye after said soft optic has been inserted therein, wherein the improvement comprises:
said collar having first and second collar ends which are in a generally overlapping relationship when said collar is compressed for insertion thereof through a small incision into an eye, and which are in a generally abutting relation when said compressible collar is in a generally uncompressed condition.

80. The intraocular lens of claim 79 wherein said collar includes a locking means for locking said first and second collar ends together when said collar is in said uncompressed condition.

81. The intraocular lens of claim 80 wherein said locking means includes a dovetail mechanism.

82. The intraocular lens of claim 79 wherein said first and second collar ends are configured relative to one another to form an interlocking dovetail arrangement when said collar is in said uncompressed condition.

83. The intraocular lens of claim 79 wherein said collar is compressible, with said attaching means attaching said soft optic to said collar, about an axis thereof and therethrough, for insertion through the small incision, and then expandable about said axis when in the eye.

84. The intraocular lens of claim 79 wherein said haptic means comprises first and second haptics attached to said collar at diagonally opposite locations thereon.

85. The intraocular lens of claim 79 wherein said soft optic includes a thickened perimeter portion adjacent said collar and into which an optic fluid varying needle can be inserted when said soft optic is remedially positioned in the eye for varying the amount of fluid in said soft optic in thereby alter the corrective power thereof, and said thickened perimeter is self sealing about the puncture opening created by said the needle as the needle is withdrawn from said soft optic.

86. The intraocular lens of claim 79 wherein said first and second collar ends slide relative to each other as said collar is compressed and uncompressed.

87. The intraocular lens of claim 79 wherein said collar has a circular shape when in said uncompressed condition.

88. The intraocular lens of claim 79 wherein said soft optic is deformed when said collar is compressed for insertion of said collar and said optic attached thereto by said attaching means through the small incision and into the eye.

89. The intraocular lens of claim 79 wherein said collar is translucent.

90. The intraocular lens of claim 79 wherein said collar has an inside surface and said attaching means comprises a plurality of spot welds spaced about said inside surface of said collar.

91. The intraocular lens of claim 79 wherein said soft optic is filled with a transparent fluid, and said soft optic includes an optic portion which is generally adjacent the periphery thereof and said collar, and which is self-sealing after the removal therefrom of an optic-fluid adjusting needle.

92. The intraocular lens of claim 79 wherein said first collar end, when said collar is compressed, slides inside of and relative to the optic axis of said soft optic and relative to said second collar end.

93. The intraocular lens of claim 79 wherein said soft optic comprises a flexible bag filled with a polymeric liquid material of gel-like consistency.

94. The intraocular lens of claim 79 wherein said haptic means comprises at least two spaced haptics extending radially out from said collar.

95. The intraocular lens of claim 94 wherein said haptic comprise at least two J-shaped loops.

96. The intraocular lens of claim 94 wherein said haptics comprise at least two flexible, resilient loops attached at their proximal ends to said collar.

* * * * *